(12) United States Patent  (10) Patent No.: US 8,388,384 B2
Cotter  (45) Date of Patent: Mar. 5, 2013

(54) BI-VENTRICULAR PERCUTANEOUS CABLE

(75) Inventor: Christopher James Cotter, Newburyport, MA (US)

(73) Assignee: Thoratec Corporation, Pleasanton, CA (US)

(*) Notice: Subject to any disclaimer, the term of this patent is extended or adjusted under 35 U.S.C. 154(b) by 0 days.

(21) Appl. No.: 13/155,009

(22) Filed: Jun. 7, 2011

(65) Prior Publication Data

US 2011/0298304 A1 Dec. 8, 2011

Related U.S. Application Data

(60) Provisional application No. 61/352,087, filed on Jun. 7, 2010.

(51) Int. Cl.
*H01R 25/00* (2006.01)
(52) U.S. Cl. ........................................... 439/638
(58) Field of Classification Search ............... 439/638, 439/668, 669, 271, 502, 909; 600/16–18
See application file for complete search history.

(56) References Cited

U.S. PATENT DOCUMENTS

| | | | | |
|---|---|---|---|---|
| 3,646,940 A * | 3/1972 | Timm et al. | | 607/40 |
| 3,724,467 A * | 4/1973 | Avery et al. | | 607/117 |
| 3,974,834 A * | 8/1976 | Kane | | 607/127 |
| 4,016,884 A * | 4/1977 | Kwan-Gett | | 604/175 |
| 4,379,462 A * | 4/1983 | Borkan et al. | | 607/117 |
| 4,495,917 A * | 1/1985 | Byers | | 607/57 |
| 4,774,952 A * | 10/1988 | Smits | | 607/2 |
| 4,955,856 A * | 9/1990 | Phillips | | 600/16 |
| 5,328,442 A * | 7/1994 | Levine | | 600/17 |
| 5,688,245 A * | 11/1997 | Runge | | 604/151 |
| 5,782,645 A * | 7/1998 | Stobie et al. | | 439/289 |
| 5,797,970 A * | 8/1998 | Pouvreau | | 607/9 |
| 6,067,474 A * | 5/2000 | Schulman et al. | | 607/57 |
| 6,132,363 A | 10/2000 | Freed et al. | | |
| 6,185,452 B1 * | 2/2001 | Schulman et al. | | 604/20 |
| 6,263,245 B1 * | 7/2001 | Snell | | 607/60 |
| 6,493,588 B1 * | 12/2002 | Malaney et al. | | 607/46 |
| 6,605,032 B2 * | 8/2003 | Benkowski et al. | | 600/16 |
| 6,725,096 B2 * | 4/2004 | Chinn et al. | | 607/115 |
| 6,802,806 B2 * | 10/2004 | McCarthy et al. | | 600/16 |
| 6,854,994 B2 * | 2/2005 | Stein et al. | | 439/218 |
| 6,876,885 B2 * | 4/2005 | Swoyer et al. | | 607/116 |
| 7,295,878 B1 * | 11/2007 | Meadows et al. | | 607/61 |
| 7,594,828 B2 * | 9/2009 | Alexander et al. | | 439/669 |
| 7,650,187 B2 * | 1/2010 | Gruber et al. | | 607/33 |
| 7,758,384 B2 * | 7/2010 | Alexander et al. | | 439/623 |
| 7,803,021 B1 * | 9/2010 | Brase | | 439/668 |

(Continued)

OTHER PUBLICATIONS

PCT Notification of Transmittal of the International Search Report and the Written Opinion for Application No. PCT/US2011/039466 dated Feb. 24, 2012, 10 pages.

(Continued)

*Primary Examiner* — Amy Cohen Johnson
*Assistant Examiner* — Vladimir Imas
(74) *Attorney, Agent, or Firm* — Fish & Richardson P.C.

(57) ABSTRACT

A percutaneous cable includes a cable body having a first end and second end, the cable body including a sheath adapted to traverse a patient's skin. The cable includes a plurality of conductors disposed within the cable body configured to transmit power and control data between a system controller and two implantable pumps. The cable includes a first connector disposed at the first end of the cable body and coupled to the plurality of conductors, the first connector configured to connect the cable body to the system controller. The cable includes a second connector disposed at the second end of the cable body, the second connector comprising a first set of contacts and a second set of contacts.

23 Claims, 6 Drawing Sheets

U.S. PATENT DOCUMENTS

| | | | |
|---|---|---|---|
| 7,824,358 B2 * | 11/2010 | Cotter et al. | 604/6.16 |
| 7,914,343 B2 * | 3/2011 | Alexander et al. | 439/669 |
| 7,962,222 B2 * | 6/2011 | He et al. | 607/61 |
| 8,055,337 B2 * | 11/2011 | Moffitt et al. | 607/2 |
| 2003/0023255 A1 * | 1/2003 | Miles et al. | 606/158 |
| 2004/0059178 A1 * | 3/2004 | McCarthy et al. | 600/16 |
| 2006/0074271 A1 * | 4/2006 | Cotter | 600/16 |
| 2007/0129779 A1 | 6/2007 | Ayre et al. | |
| 2008/0208267 A1 * | 8/2008 | Alexander et al. | 607/2 |
| 2011/0093034 A1 | 4/2011 | Kast et al. | |
| 2011/0160516 A1 | 6/2011 | Dague et al. | |

OTHER PUBLICATIONS

Medtronic, "Extension Dual quadripolar extension kit (8-2-4)," Implant manual, #37082, Sep. 2005, 15 pages.

* cited by examiner

__US 8,388,384 B2__

BI-VENTRICULAR PERCUTANEOUS CABLE

CROSS-REFERENCE TO RELATED APPLICATION

This application claims priority from U.S. Provisional Application No. 61/352,087, filed Jun. 7, 2010, and titled "BI-VENTRICULAR PERCUTANEOUS CABLE," which is incorporated by reference.

TECHNICAL FIELD

This disclosure relates to a percutaneous cable for mechanical circulatory cardiac assist devices.

BACKGROUND

Heart assist devices or pumps can be inserted in the circulatory system to pump blood from the ventricle to the vasculature. Such a pump is known as a ventricular assist device, or VAD. A VAD is useful when the ventricle alone is incapable of providing adequate blood flow.

Two implantable VADs, each with associated pump control equipment, have typically been used to provide bi-ventricular support for heart failure patients.

SUMMARY

Rather than requiring two sets of pump control equipment to control two VADs, a single integrated percutaneous cable simultaneously and independently transmits power and control data between, for example, a universal system controller positioned outside a human body, and two implanted VADs. The single integrated percutaneous cable controls the two implanted VADs independently, without the need for two sets of system drivers, percutaneous cables, and power management components. Use of a single percutaneous cable further eliminates at least one incision and entry point into the human body, which reduces a patient's cable and wound management burdens.

In a general aspect, a percutaneous cable includes a cable body having a first end and a second end. The cable body includes a sheath adapted to traverse a patient's skin. The cable includes a plurality of conductors disposed within the cable body configured to transmit power and control data between a system controller and two implantable pumps. The cable also includes a first connector disposed at the first end of the cable body and coupled to the plurality of conductors, the first connector configured to connect the cable body to the system controller, and a second connector disposed at the second end of the cable body. The second connector includes a first set of contacts and a second set of contacts, the first set of contacts coupled to a first portion of the plurality of conductors and adapted to electrically connect the first portion of the plurality of conductors to a first of the two implantable pumps and the second set of contacts coupled to a second portion of the plurality of conductors and adapted to electrically connect the second portion of the plurality of conductors to a second of the two implantable pumps. The second connector includes a first end that has an inner surface, the inner surface of the first end being configured to interact with respective sealing members of a first pump cable when the first pump cable is coupled to the first end of the second connector. The second connector includes a second end having an inner surface, the inner surface of the second end being configured to interact with respective sealing members of a second pump cable when the second pump cable is coupled to the second end of the second connector.

Implementations may include one or more of the following features. For example, the second connector is made from a biocompatible material and is implantable beneath the skin. The first end of the second connector includes a threaded outer surface that is configured to mate with an inner threaded surface of a first screw ring surrounding at least a part of the first pump cable, and the second end of the second connector includes a threaded outer surface that is configured to mate with an inner threaded surface of a second screw ring surrounding at least a part of the second pump cable. The sealing members include o-rings. The inner surface of the first end includes two portions having different diameters, and the inner surface of the second end includes two portions having different diameters. The first portion of the plurality of conductors are hard wired to the first set of contacts and the first set of contacts includes a plurality of receptacles configured to receive mating pins of a first pump cable when the first pump cable is coupled to the first end of the second connector, and the second portion of the plurality of conductors are hard wired to the second set of contacts and the second set of contacts includes a plurality of receptacles configured to receive mating pins of a second pump cable when the second pump cable is coupled to the second end of the second connector. The second connector further includes a first end having a threaded outer surface and an inner surface, the inner surface of the first end being configured to interact with respective sealing members of a first pump cable when the first pump cable is coupled to the first end of the second connector, and a second end coupled to a second pump cable.

In another aspect, an implantable connector includes a housing made from a biocompatible material. The housing includes a first connector having a threaded outer surface and an inner surface having a first diameter and a second diameter less than the first diameter. The inner surface of the first connector is configured to interact with respective sealing members of a percutaneous cable when the percutaneous cable is coupled to the first connector. The percutaneous cable includes a first set of conductors for transmitting power and control data between a controller and two implantable pumps. The housing includes a second connector having a threaded outer surface and an inner surface having a first diameter and a second diameter less than the first diameter. The inner surface of the second connector is configured to interact with respective sealing members of a first pump cable when the first pump cable is coupled to the second connector. The first pump cable includes a second set of conductors for transmitting power and control data between the controller and a first of the two implantable pumps. The housing includes a third connector having a threaded outer surface and an inner surface having a first diameter and a second diameter less than the first diameter. The inner surface of the third connector is configured to interact with respective sealing members of a second pump cable when the second pump cable is coupled to the third connector. The second pump cable includes a third set of conductors for transmitting power and control data between the controller and a second of the two implantable pumps. The housing includes a first contact block disposed within the first connector, the first contact block including a plurality of electrical contacts that are configured to connect to the first set of conductors in the percutaneous cable when the percutaneous cable is coupled to the first connector. The housing includes a second contact block disposed within the second connector, the second contact block including a plurality of electrical contacts that are connected to a first portion of the contacts of the first contact block and are configured to connect to the second set of conductors in the first pump cable when the first pump cable is coupled to the second connector. The housing includes a third contact block disposed within the third connector, the third contact block including a plurality of electrical contacts that are connected to a second portion of the contacts of the first contact block and are configured to connect to the third set of conductors in the second pump cable when the second pump cable is coupled to the third connector.

Implementations may include one or more of the following features. For example, the threaded outer surface of the first connector is configured to mate with an inner threaded surface of a first screw ring surrounding at least a part of the percutaneous cable. The threaded outer surface of the second connector is configured to mate with an inner threaded surface of a second screw ring surrounding at least a part of the first pump cable, and the threaded outer surface of the first connector is configured to mate with an inner threaded surface of a third screw ring surrounding at least a part of the second pump cable. The electrical contacts of the second contact block are hard wired to the first portion of the contacts of the first contact block and the electrical contacts of the third contact block are hard wired to the second portion of the contacts of the first contact block. The first, second, and third contact blocks each include a plurality of receptacles configured to receive mating pins of the percutaneous cable, first pump cable, and second pump cable, respectively.

In another general aspect, a method includes transmitting power and control data from a controller through a plurality of conductors of a percutaneous cable, bifurcating the power and control data from the plurality of conductors of the percutaneous cable onto a first set of conductors and a second set of conductors via a connector implanted with a body, transmitting power and control data through the first set of conductors to a first pump cable connected to a first of two implanted ventricular assist pumps, and transmitting power and control data through the second set of conductors to a second pump cable connected to a second of the two implantable ventricular assist pumps.

Implementations may include one or more of the following features. For example, the percutaneous cable includes a biocompatible sheath that is adapted to traverse skin. The percutaneous cable traverses skin and is releasably connected to the connector implanted within the body. One of the first and second pump cables is releasably connected to the connector and the other of the first and second pump cables is permanently connected to the connector. The method can also include coupling a second connector between the percutaneous cable and the controller.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
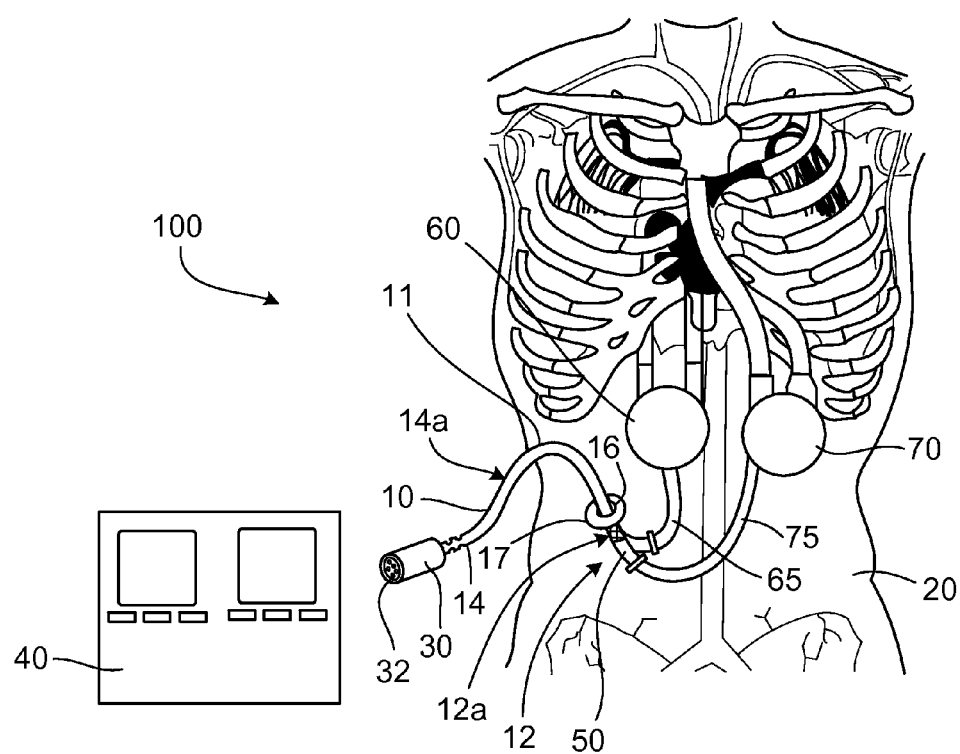
FIG. 1 illustrates a percutaneous cable and connector assembly disposed within a body.

Referring to FIG. 1, a single integrated percutaneous lead or cable 10 that is part of a heart assist system 100 includes a cable body 11, a connector 30 at an end 14 for coupling the cable 10 to a system controller 40, and a bifurcated connector 50 at an end 12 for coupling the cable 10 to two ventricular assist devices (VADs) 60, 70 via two cables 65, 75, respectively. In use, the cable 10 extends through a patient's skin with a region 12a of the cable 10 located internal to the patient's body 20, a region 14a of the cable 10 located external to the body 20, and a portion 16 extending through a single incision in the skin.

Figure 2:
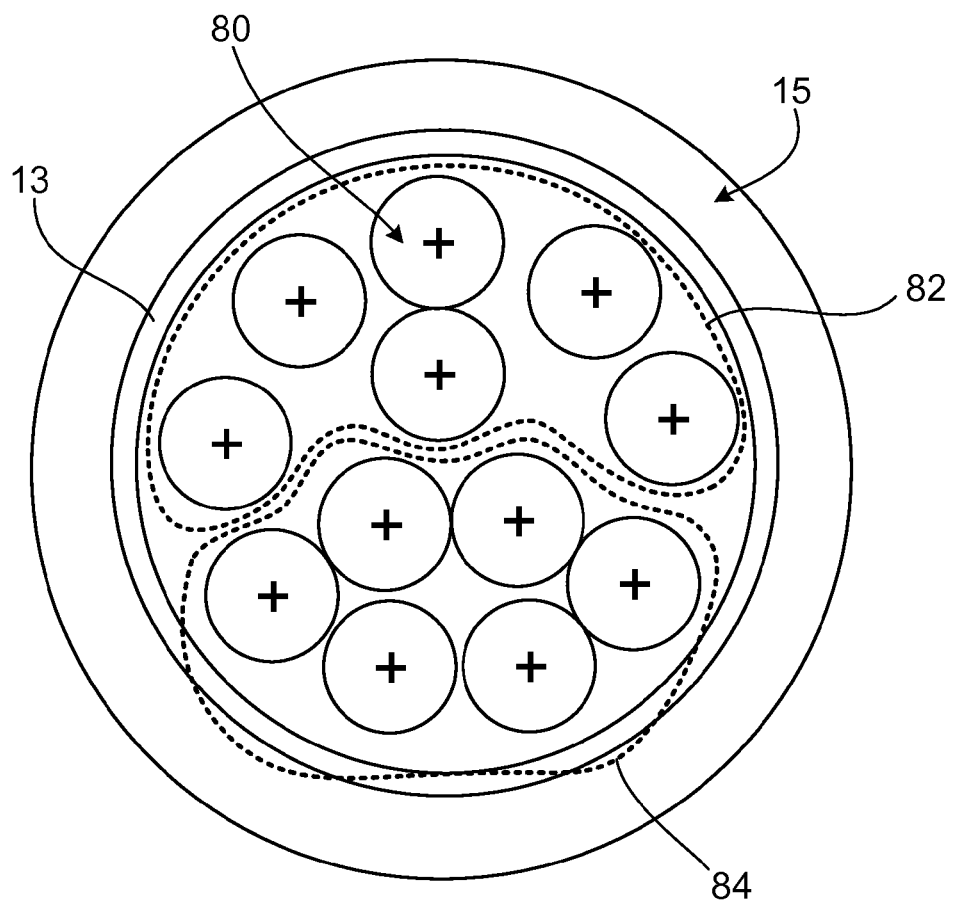
FIG. 2 is a cross-sectional view of an implementation of the percutaneous cable.

Referring to FIGS. 1 and 2, the cable 10 includes a number of conductors or wires 80 surrounded by a conductor wrap 13. The cable 10 also includes a sheath 15 formed around the conductor wrap 13. The sheath 15 is made from a material that is resistant to fluid penetration through the material. The cable 10 includes a total of twelve conductors 80, which can be, for example, further divided into two, six-conductor bundles 82, 84. Bundles 82, 84 transmit power and control data between the system controller 40 and the implanted VADs 60, 70, as will be described in further detail below. The conductor wrap 13 and sheath 15 are made from a flexible material and extend along the entire length of the conductors 80. In addition to being resistant to fluid penetration, the sheath 15 may be formed from a biocompatible material along at least a portion of its length, and particularly, along the length of the sheath 15 that will be implanted in the body or come into contact with the skin.

The connector 30 includes a number of conductive elements 32 (FIG. 1), e.g., in the form of pins or receptacles, that mate with corresponding elements (not shown) on the system controller 40. An exemplary system controller for use with the present disclosure is described in co-pending U.S. application Ser. No. 61/366,757, filed Jul. 22, 2010, the entirety of which is incorporated herein by reference. The conductive elements 32 are also connected to the conductors 80 within cable 30 in order to transmit the power and control data from the system controller 40 to the conductors 80. The conductive elements 32 are connected to the conductors 80 by any known method, including soldering, welding, crimping, and contact and/or terminal attachments.

Figure 3:
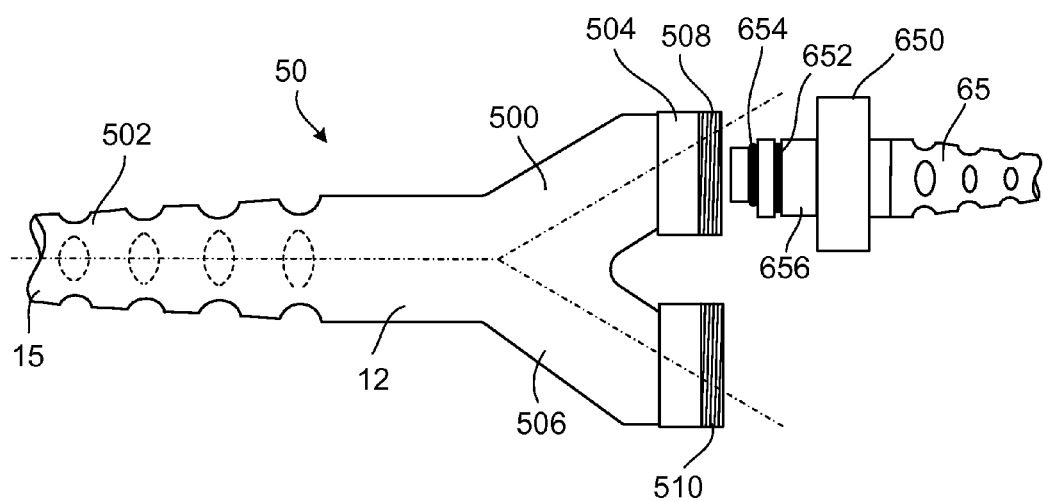
FIG. 3 illustrates a detailed exploded view of a connection between a bifurcated connector and an implantable pump cable.
Figure 4:
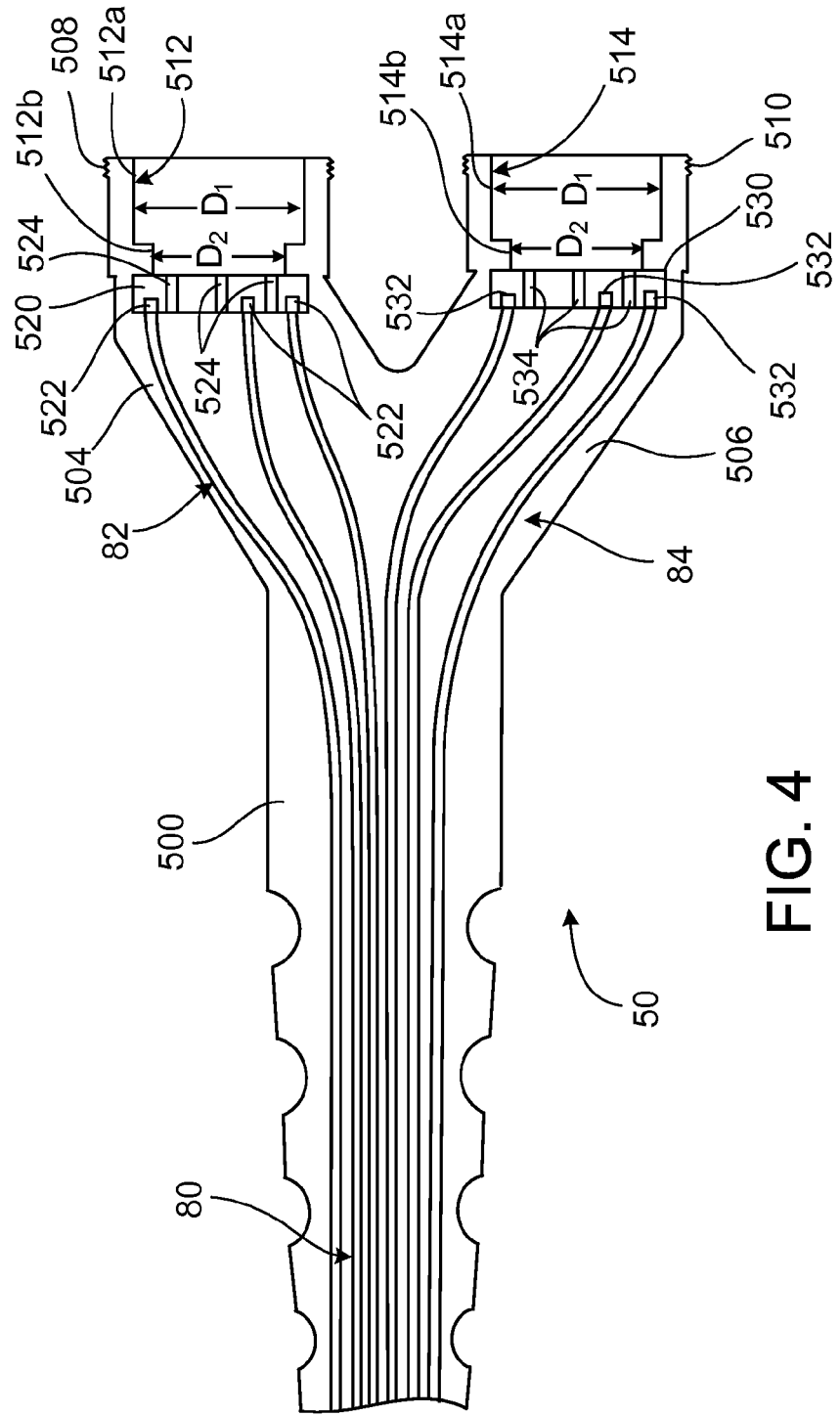
FIG. 4 is a cross-sectional view of the bifurcated connector of FIG. 3.

Referring now to FIGS. 1, 3, and 4, in use, the connector 50 includes a Y-shaped housing 500 made from a biocompatible material. The housing 500 is formed, e.g., as an overmolded projection of the cable 10, and includes a strain relief portion 502 that extends along a portion of the cable 10 away from the housing 500. The strain relief 502 minimizes any forces or stresses on conductors 80 as the cable 10 transitions from the flexible sheath 15 to the overmolded housing 500 of the connector 50.

The housing 500 includes at least two ends 504, 506 that are used to bifurcate or split the conductors 80 into the two conductor bundles 82, 84 (a portion of which are shown in the cross-sectional view of FIG. 4). Each of the ends 504, 506 are connectable to pump cables 65, 75, respectively. The pump cables 65, 75 terminate at each respective blood pump or VAD 60, 70. Specifically, each end 504, 506 includes external threads 508, 510, respectively, formed at an outer edge of the ends 504, 506. Each of the external threads 508, 510 receives a mating thread (not shown) formed in a screw ring 650 that is rotatably connected about a connector 656 of pump cables 65, 75. Only one of the screw ring 605 and connector 656 are shown in FIG. 3 for simplicity. The screw ring 650 permits the pump cables 65, 75 to be releasably connected to the housing 500.

In order to provide a seal between the housing 500 and the mating pump cables 65, 75 that limits or prevents fluid ingress, during use, the ends 504, 506 include an inner surface 512, 514 that mates with sealing members 652, 654, such as double o-rings 652, 654, disposed on connectors 656 of the pump cables 65, 75. Specifically, inner surface 512 includes a first surface 512a, defining a circular cross-sectional area having a diameter D1. Inner surface 512 includes a second surface 512b, defining a circular cross-sectional area having a diameter D2, which is less than D1. The first and second surfaces 512a, 512b interact with sealing member 652, 654, respectively, to provide a fluid-tight seal between the housing 500 and pump cable 65 when the pump cable 65 is secured to the housing 500 using, for example, the screw ring 650. Similarly, inner surface 514 includes first and second surfaces 514a and 514b that interact with sealing members (not shown) formed on the corresponding connector (not shown) of pump cable 75.

As noted above, the housing 500 includes at least two ends 504, 506 that are used to bifurcate or split the conductors 80 into the two conductor bundles 82, 84 (for simplicity, only three of the six conductors in each of conductor bundles 82, 84 are shown in FIG. 4). To accommodate this bifurcation, each end 504, 506 also includes a contact block 520, 530, respectively. Each of the contact blocks 520, 530 includes a set of electrical contacts 522, 532, respectively, that electrically connect to each of the conductors in the conductor bundles 82, 84. For example, there are six conductors in each conductor bundle 82, 84, and six corresponding contacts 522, 532 in each contact block 520, 530, although any number of conductors and respective contacts may be used depending on the implementation. The contact blocks 520, 530 also include a set of receptacles 524, 534, respectively, that receive and/or mate with corresponding electrical contact pins (not shown) formed or disposed in the end of connector 656 of the pump cables 65, 75 when the pump cables 65, 75 are connected to the housing 500 as described above.

In use, the single percutaneous cable 10 transmits power and control data between, for example, a universal controller, such as system controller 40 and two implantable blood pumps, such as VADs 60, 70. The cable 10 requires only one incision to be made in the skin of the patient, which reduces the possibility for tissue infection and reduces the complexity and amount of equipment the patient must use on a daily basis. The implantable housing 500 provides for the bifurcation of the electrical conductors from the single integrated percutaneous cable 10 to a set of dedicated pump cables, such as cables 65, 75 which are connected to the implanted VADs 60, 70. The sealing and connections between the pump cables 65, 75 and the bifurcated ends 504, 506 of the housing 500 facilitate disconnecting the percutaneous lead 10 from the VADs 60, 70 for maintenance, cleaning, etc.

Figure 5:
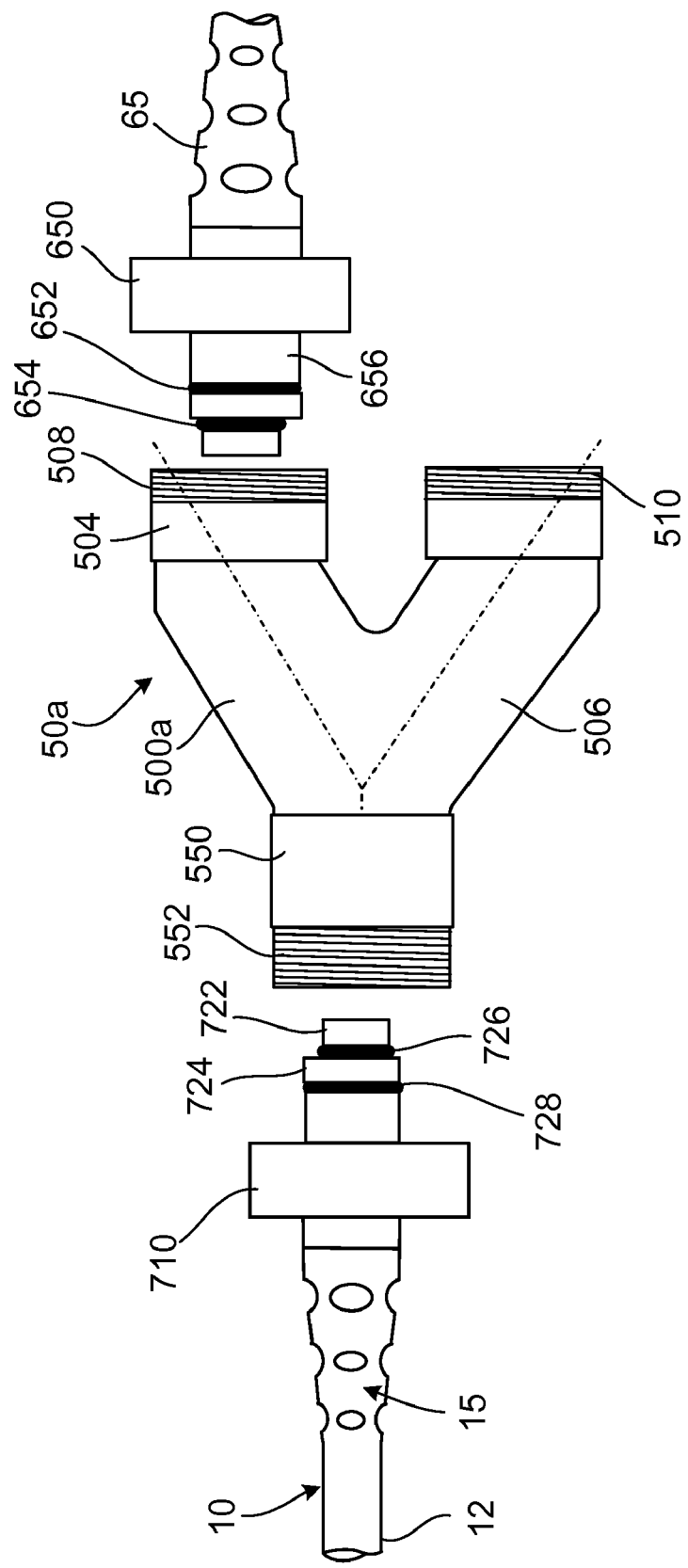
FIG. 5 illustrates an alternative implementation of the percutaneous cable and bifurcated connector, and an exemplary connection between the percutaneous cable, bifurcated connector, and implantable pump cables.
Figure 6:
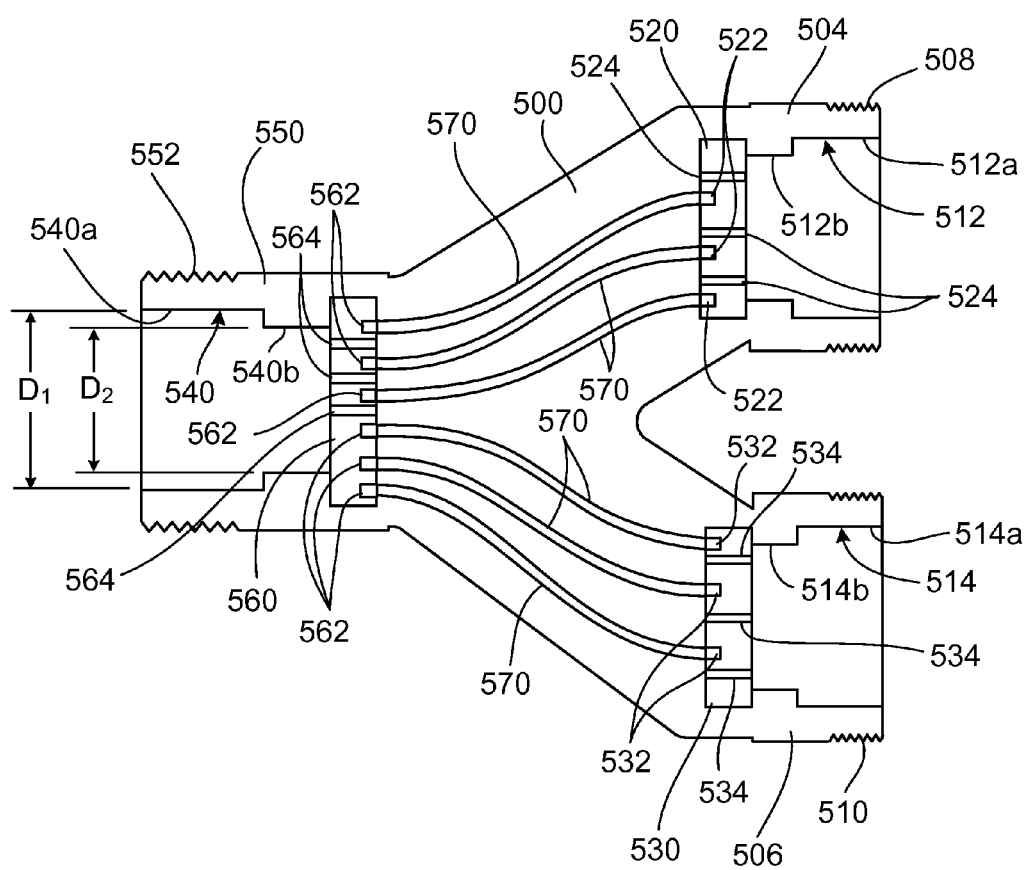
FIG. 6 is a cross-sectional view of the bifurcated connector of FIG. 5.

In an alternative implementation, instead of being formed as an overmolded projection of the cable 10, the connector 50a of FIGS. 5 and 6 includes a housing 500a that is removably connectable to both the percutaneous cable 10 as well as the pump cables 65, 75. The connections between the housing 500a and the pump cables 65, 75 have been described above with reference to the implementation of FIGS. 3 and 4, and therefore, for the sake of brevity will not be repeated here.

In addition to ends 504, 506, which were described above, the housing 500a includes an additional end 550, which connects to the percutaneous cable 10. In this example, the cable 10 includes a connector 700 that is constructed in a similar manner to, for example, connector 656 of pump cables 65, 75. In particular, the connector 700 includes a screw ring 710 having internal threads (not shown) rotatably secured about the connector 700 and a male connector socket 720 that includes a first section 722 having a cross-sectional area and a second section 724 having a cross-sectional area that is larger than the cross-sectional area of the first section 722. Sections 722, 724 are preferably circular, but other geometric shapes may be employed, such as square, rectangular, semi-circular, etc. One exemplary purpose of a non-uniform geometric shape is to ensure proper orientation of the connectors for electrical connections. Alternately, the sections 722, 724 may employ another feature or element for ensuring proper electrical connections. Received in each of sections 722, 724 are sealing members, such as, for example, o-rings 726, 728, respectively. The connector 700 includes a set of electrical contact pins (not shown) formed or disposed in the end of connector 700 of the percutaneous cable 10. The contact pins are connected to the conductors 80 within the percutaneous cable 10 by any known method, including soldering, welding, crimping, or using an appropriate contact and/or terminal attachments. In this exemplary implementation, there are a total of, for example, twelve contact pins, each corresponding to the twelve conductors 80 disposed in the percutaneous cable 10. The proximal end 12 of cable 10 includes a strain relief portion 15 at the proximal end 12 of the cable 10. The strain relief 15 minimizes any forces or stresses on conductors 80 as the cable 10 transitions from the flexible sheath 15 to the connector 700.

The end 550 of the connector 50a is releasably connected to the connector 700 of the percutaneous cable 10. Specifically, the end 550 includes external threads 552 formed at an outer edge of the end 550. The external threads 552 receive the internal threads (not shown) of the screw ring 710 of the connector 700. In order to provide a seal between the end 550 and the mating connector 700, the end 550 includes an inner surface 540 that mates with sealing members, such as the double o-rings 726, 728. Specifically, inner surface 540 includes a first surface 540a, defining a circular cross-sectional area having a diameter D1, and a second surface 540b, defining a circular cross-sectional area having a diameter D2, which is smaller than D1. The first and second surfaces 540a, 540b interact with sealing members 728, 726, respectively, to provide a seal between the housing 500a and percutaneous cable 10 when the percutaneous cable 10 is secured to the housing 500a using, for example, the screw ring 710.

In order to bifurcate or split the control and power data from the respective conductors 80 and transmit the control and power data to the appropriate implanted pump, along for example, pump cables 65, 75, the end 550 includes a contact block 560. The contact block 560 includes a set of receptacles 564 that receive and/or mate with the corresponding electrical contact pins (not shown) formed or disposed in the end of connector 700 of the percutaneous cable 10 when the percutaneous cable 10 is connected to the housing 500a. In this particular example, the contact block 560 includes twelve receptacles corresponding to the twelve conductors 80 disposed in the percutaneous cable 10. Any number of receptacles may be included in the contact block 560. The contact block 560 further includes a set of electrical contacts 562, each of which are connected to a number of conductors or wires 570 (a portion of which are shown in FIG. 6). A portion of the conductors or wires 570 are likewise connected to the contacts formed in each of the contact blocks 520, 530 in order to bifurcate the power and control data and/or other electrical signals for the appropriate pump 60, 70. For example, in the exemplary implementation, twelve wires or conductors 80 are connected to the contact block 560 of the housing 500a via the connector 700 of the percutaneous cable 10. Six wires or conductors 570 are connected between the contact block 560 and the contact block 520 and six wires or conductors 570 are connected between the contact block 560 and the contact block 530. In this manner, control, power, and/or other electrical information can be delivered through the single percutaneous cable 10, bifurcated within the connector 50a and be transmitted to the appropriate implanted pump via, for example, the connected pump cables 65, 75 as described above.

In use, the modularity of the bifurcated connector 50a of FIGS. 5 and 6 provides the user with the ability to change only the percutaneous lead, for example, in case the lead becomes unusable. This could be advantageous given that the diameter of the cable in certain implementations is smaller than the size of the bifurcated connector and therefore may provide the ability to replace the cable with a less-intrusive operation.

The percutaneous lead 10 can additionally include other features that reduce a user's possibility of infection and/or provide stabilization of the percutaneous lead 10 with respect to the body 20. As described above, an opening in the skin exposes tissue to infection. Additionally, movement of the portion 16 of the percutaneous lead 10 that traverses the skin opening in relation to the skin opening itself can cause damage to tissue surrounding the percutaneous lead 10, thus increasing the possibility of infection. The percutaneous lead can include features that reduce movement of the internal portion of the percutaneous lead 10 relative to the user. An exemplary system for reducing movement of the lead relative to the user and for use with the present disclosure is described in co-pending U.S. application Ser. No. 61/375,766, filed Aug. 20, 2010, the entirety of which is incorporated herein by reference. In addition, as shown in FIG. 1, the percutaneous lead 10 can include a strain-relief portion 17 for anchoring the percutaneous lead 10 to the user and for reducing the strain on the portion of the percutaneous lead exiting the user's body. Although the strain-relief portion 17 is shown on the outside of the body 20, an appropriate strain-relief portion may be provided under the skin or elsewhere in the body.

A number of implementations have been described. Nevertheless, it will be understood that various modifications may be made without departing from the spirit and scope of the disclosure. For example, while twelve conductors 80 have been shown disposed in the percutaneous cable 10 and leading from the system controller 40, and six conductors in each of the pump cables 65, 75, it will be apparent that more or less conductors may be employed depending on the power and control characteristics of the heart assist devices to be controlled. In addition, although the cable 10 has been described as being divided into two, six-conductor bundles 82, 84, any number of suitable bundles may be employed. Further, although bundles 82, 84 have been described as transmitting power and control data between the system controller 40 and the implanted VADs 60, 70, the cables/bundles can be used for other types of electrical signal transmission. In addition, although the conductor wrap 13 and sheath 15 have been described as extending along the entire length of the conductors 80, other implementations may include the conductor wrap 13 or the sheath 15 extending along a portion, but not all, of the length of the conductors.

In addition, although the screw rings 650, 710 have been described as the means of coupling the various cables to the implantable bifurcated housing, other connectors may be used. Examples of such connectors may include twist-and-lock connectors, connectors with bolted flanges, compressive fittings, or other threaded connections. Further, the screw rings may also be provided with appropriate locking features that prevent them from loosening during use. In addition, although sealing members have been described as double o-rings 652 or o-rings 726, 728, other sealing devices may be used. Examples of such sealing members may include chevron seals, u-cups, diaphragms, discs, sleeves, or other suitable elastomeric, metallic, or plastic seals.

Further, although the implementations have been described as employing a single bifurcated implantable connector, the system can also employ an external bifurcated connector to allow, for example, two separate system controllers to be used. This may allow for less complex system controllers to be employed even though the number of controllers is increased. In addition, the bifurcated connector may be made from a non-biocompatible material, in which case, the connector would be disposed outside of the patient's body. Such a connector may be made from, for example, less expensive materials, and perhaps would not require the same fluid-tight fittings and arrangements as described above, however, such a connector may require the use of two incisions in the body for the passage of two pump cables. In another implementation, instead of having two ends or passageways 508, 510 connectable to pump cables, such as pump cables 65, 75, one of the ends or passageways may be permanently connected to one of the pump cables.

Further, although, for example, the inner surfaces of the ends or pathways 504, 506 and 550 of the bifurcated connector housing have been described as defining circular cross-sectional area, other geometric shapes are possible, including, for example, square, rectangular, semicircular, or other suitable shapes. Further, while the connector 50 has been described as including a Y-shaped housing 500 made from a biocompatible material, the housing can be any suitable shape, such as, for example, X-shaped if the cable needs, for example, to be in a bifurcated configuration for electrically coupling to two different devices (e.g., power source and controller are separate).

In addition, the connector 30 may include a cap (not shown) used to protect the external physical structure of the distal end 14 and the connector 30, as well as the exposed metal conductive elements 32 that can be coupled to the system controller 40. In some implementations, this cap can be designed to be fluid resistant or fluid proof. In other implementations, the cap can prevent moisture from seeping into the connector and reaching the metal connections. The cap can also limit any electrical conduction from any outside element with the metal connections.

The various parts of the system may be constructed from any appropriate and adequately durable materials. For example, the connectors and other structural components may be made from titanium or titanium alloy, stainless steel, or a plastic of appropriate strength that is capable of long-term implantability and sterilization, as necessary.

Accordingly, other embodiments are within the scope of the following claims.

What is claimed is:
1. A percutaneous cable comprising:
a cable body having a first end and second end, the cable body comprising a sheath adapted to traverse a patient's skin;

a plurality of conductors disposed within the cable body configured to transmit power between a system controller and two implantable pumps;

a first connector disposed at the first end of the cable body and coupled to the plurality of conductors, the first connector configured to connect the cable body to the system controller; and a second connector disposed at the second end of the cable body, the second connector comprising:

a first set of contacts and a second set of contacts, the first set of contacts coupled to a first portion of the plurality of conductors and adapted to electrically connect the first portion of the plurality of conductors to a first of the two implantable pumps and the second set of contacts coupled to a second portion of the plurality of conductors and adapted to electrically connect the second portion of the plurality of conductors to a second of the two implantable pumps, a first end having an inner surface, the inner surface of the first end being configured to interact with respective sealing members of a first pump cable when the first pump cable is coupled to the first end of the second connector, and a second end having an inner surface, the inner surface of the second end being configured to interact with respective sealing members of a second pump cable when the second pump cable is coupled to the second end of the second connector, wherein the first end of the second connector comprises a threaded outer surface that is configured to mate with an inner threaded surface of a first screw ring surrounding at least a part of the first pump cable, and wherein the second end of the second connector comprises a threaded outer surface that is configured to mate with an inner threaded surface of a second screw ring surrounding at least a part of the second pump cable.

2. The cable of claim 1, wherein the second connector is made from a biocompatible material and is implantable beneath the skin.

3. The cable of claim 1, wherein the sealing members comprise o-rings.

4. The cable of claim 1, wherein the inner surface of the first end comprises two portions having different diameters, and the inner surface of the second end comprises two portions having different diameters.

5. The cable of claim 1, wherein the first portion of the plurality of conductors are hard wired to the first set of contacts and the first set of contacts comprises a plurality of receptacles configured to receive mating pins of a first pump cable when the first pump cable is coupled to the first end of the second connector, and wherein the second portion of the plurality of conductors are hard wired to the second set of contacts and the second set of contacts comprises a plurality of receptacles configured to receive mating pins of a second pump cable when the second pump cable is coupled to the second end of the second connector.

6. The cable of claim 1, wherein the second connector further comprises:

a first end having a threaded outer surface and an inner surface, the inner surface of the first end being configured to interact with respective sealing members of a first pump cable when the first pump cable is coupled to the first end of the second connector; and a second end coupled to a second pump cable.

7. The cable of claim 1, further comprising a cap received on the first connector.

8. An implantable connector comprising:

a housing made from a biocompatible material, the housing comprising:

a first connector having a threaded outer surface and an inner surface having a first diameter and a second diameter less than the first diameter, the inner surface of the first connector configured to interact with respective sealing members of a percutaneous cable when the percutaneous cable is coupled to the first connector, the percutaneous cable comprising a first set of conductors for transmitting power between a controller and two implantable pumps;

a second connector having a threaded outer surface and an inner surface having a first diameter and a second diameter less than the first diameter, the inner surface of the second connector configured to interact with respective sealing members of a first pump cable when the first pump cable is coupled to the second connector, the first pump cable comprising a second set of conductors for transmitting power between the controller and a first of the two implantable pumps;

a third connector having a threaded outer surface and an inner surface having a first diameter and a second diameter less than the first diameter, the inner surface of the third connector configured to interact with respective sealing members of a second pump cable when the second pump cable is coupled to the third connector, the second pump cable comprising a third set of conductors for transmitting power between the controller and a second of the two implantable pumps;

a first contact block disposed within the first connector, the first contact block comprising a plurality of electrical contacts that are configured to connect to the first set of conductors in the percutaneous cable when the percutaneous cable is coupled to the first connector;

a second contact block disposed within the second connector, the second contact block comprising a plurality of electrical contacts that are connected to a first portion of the contacts of the first contact block and are configured to connect to the second set of conductors in the first pump cable when the first pump cable is coupled to the second connector; and a third contact block disposed within the third connector, the third contact block comprising a plurality of electrical contacts that are connected to a second portion of the contacts of the first contact block and are configured to connect to the third set of conductors in the second pump cable when the second pump cable is coupled to the third connector.

9. The connector of claim 8, wherein the threaded outer surface of the first connector is configured to mate with an inner threaded surface of a first screw ring surrounding at least a part of the percutaneous cable, the threaded outer surface of the second connector is configured to mate with an inner threaded surface of a second screw ring surrounding at least a part of the first pump cable, and the threaded outer surface of the first connector is configured to mate with an inner threaded surface of a third screw ring surrounding at least a part of the second pump cable.

10. The connector of claim 8, wherein the electrical contacts of the second contact block are hard wired to the first portion of the contacts of the first contact block and the electrical contacts of the third contact block are hard wired to the second portion of the contacts of the first contact block.

11. The connector of claim 8, wherein the first, second, and third contact blocks each comprise a plurality of receptacles configured to receive mating pins of the percutaneous cable, first pump cable, and second pump cable, respectively.

12. A percutaneous cable comprising:
a cable body having a first end and second end, the cable body comprising a sheath adapted to traverse a patient's skin;
a plurality of conductors disposed within the cable body configured to transmit power between a system controller and two implantable pumps;
a first connector disposed at the first end of the cable body and coupled to the plurality of conductors, the first connector configured to connect the cable body to the system controller; and
a second connector disposed at the second end of the cable body, the second connector comprising:
a first set of contacts and a second set of contacts, the first set of contacts coupled to a first portion of the plurality of conductors and adapted to electrically connect the first portion of the plurality of conductors to a first of the two implantable pumps and the second set of contacts coupled to a second portion of the plurality of conductors and adapted to electrically connect the second portion of the plurality of conductors to a second of the two implantable pumps,
a first end having an inner surface, the inner surface of the first end being configured to interact with respective sealing members of a first pump cable when the first pump cable is coupled to the first end of the second connector, and
a second end having an inner surface, the inner surface of the second end being configured to interact with respective sealing members of a second pump cable when the second pump cable is coupled to the second end of the second connector,
wherein the inner surface of the first end comprises two portions having different diameters, and the inner surface of the second end comprises two portions having different diameters.

13. The cable of claim 12, wherein the second connector is made from a biocompatible material and is implantable beneath the skin.

14. The cable of claim 12, wherein the sealing members comprise o-rings.

15. The cable of claim 12, further comprising a cap received on the first connector.

16. A percutaneous cable comprising:
a cable body having a first end and second end, the cable body comprising a sheath adapted to traverse a patient's skin;
a plurality of conductors disposed within the cable body configured to transmit power between a system controller and two implantable pumps;
a first connector disposed at the first end of the cable body and coupled to the plurality of conductors, the first connector configured to connect the cable body to the system controller; and
a second connector disposed at the second end of the cable body, the second connector comprising:
a first set of contacts and a second set of contacts, the first set of contacts coupled to a first portion of the plurality of conductors and adapted to electrically connect the first portion of the plurality of conductors to a first of the two implantable pumps and the second set of contacts coupled to a second portion of the plurality of conductors and adapted to electrically connect the second portion of the plurality of conductors to a second of the two implantable pumps,
a first end having an inner surface, the inner surface of the first end being configured to interact with respective sealing members of a first pump cable when the first pump cable is coupled to the first end of the second connector, and
a second end having an inner surface, the inner surface of the second end being configured to interact with respective sealing members of a second pump cable when the second pump cable is coupled to the second end of the second connector,
wherein the first portion of the plurality of conductors are hard wired to the first set of contacts and the first set of contacts comprises a plurality of receptacles configured to receive mating pins of a first pump cable when the first pump cable is coupled to the first end of the second connector, and wherein the second portion of the plurality of conductors are hard wired to the second set of contacts and the second set of contacts comprises a plurality of receptacles configured to receive mating pins of a second pump cable when the second pump cable is coupled to the second end of the second connector.

17. The cable of claim 16, wherein the second connector is made from a biocompatible material and is implantable beneath the skin.

18. The cable of claim 16, wherein the sealing members comprise o-rings.

19. The cable of claim 16, further comprising a cap received on the first connector.

20. A percutaneous cable comprising:
a cable body having a first end and second end, the cable body comprising a sheath adapted to traverse a patient's skin;
a plurality of conductors disposed within the cable body configured to transmit power between a system controller and two implantable pumps;
a first connector disposed at the first end of the cable body and coupled to the plurality of conductors, the first connector configured to connect the cable body to the system controller; and
a second connector disposed at the second end of the cable body, the second connector comprising:
a first set of contacts and a second set of contacts, the first set of contacts coupled to a first portion of the plurality of conductors and adapted to electrically connect the first portion of the plurality of conductors to a first of the two implantable pumps and the second set of contacts coupled to a second portion of the plurality of conductors and adapted to electrically connect the second portion of the plurality of conductors to a second of the two implantable pumps,
a first end having an inner surface, the inner surface of the first end being configured to interact with respective sealing members of a first pump cable when the first pump cable is coupled to the first end of the second connector, and
a second end having an inner surface, the inner surface of the second end being configured to interact with respective sealing members of a second pump cable when the second pump cable is coupled to the second end of the second connector,
wherein the second connector further comprises:
a first end having a threaded outer surface and an inner surface, the inner surface of the first end being configured to interact with respective sealing members of a first pump cable when the first pump cable is coupled to the first end of the second connector; and a second end coupled to a second pump cable.

21. The cable of claim 20, wherein the second connector is made from a biocompatible material and is implantable beneath the skin.

22. The cable of claim 20, wherein the sealing members comprise o-rings.

23. The cable of claim 20, further comprising a cap received on the first connector.

* * * * *